United States Patent
Muhl et al.

(10) Patent No.: US 11,007,521 B2
(45) Date of Patent: May 18, 2021

(54) ANALYSIS METHOD, DISCOID SAMPLE HOLDER AND USE OF A SAMPLE HOLDER

(71) Applicant: Testo SE & Co. KGaA, Lenzkirch (DE)

(72) Inventors: Mike Muhl, Freiburg i. Brsg. (DE); Simon Brugger, Lenzkirch (DE); Martin Zubler, Lenzkirch (DE)

(73) Assignee: TESTO SE & CO. KGAA, Lenzkirch (DE)

( * ) Notice: Subject to any disclaimer, the term of this patent is extended or adjusted under 35 U.S.C. 154(b) by 308 days.

(21) Appl. No.: 15/538,929

(22) PCT Filed: Dec. 23, 2015

(86) PCT No.: PCT/EP2015/002612
§ 371 (c)(1),
(2) Date: Jun. 22, 2017

(87) PCT Pub. No.: WO2016/102071
PCT Pub. Date: Jun. 30, 2016

(65) Prior Publication Data
US 2017/0348689 A1    Dec. 7, 2017

(30) Foreign Application Priority Data
Dec. 23, 2014 (DE) .......................... 102014019526.0

(51) Int. Cl.
*B01L 3/00* (2006.01)
*G01N 1/31* (2006.01)
(Continued)

(52) U.S. Cl.
CPC ........ *B01L 3/502715* (2013.01); *A61B 10/02* (2013.01); *B01L 3/5029* (2013.01);
(Continued)

(58) Field of Classification Search
CPC ............... B01L 3/502715; B01L 3/561; B01L 3/50273; B01L 3/5029; B01L 2200/028; B01L 2300/069; B01L 2300/0803; B01L 2400/0409; G01N 1/08; G01N 1/10; G01N 1/31; G01N 33/4875; A61B 10/02
(Continued)

(56) References Cited

U.S. PATENT DOCUMENTS

| 6,582,912 B1 | 6/2003 | Rousseau et al. |
| 2005/0059165 A9 * | 3/2005 | Davis ................. A61B 10/0045 436/514 |

(Continued)

FOREIGN PATENT DOCUMENTS

| CN | 200978283 | 11/2007 |
| EP | 1188482 | 3/2002 |

(Continued)

*Primary Examiner* — Matthew D Krcha
*Assistant Examiner* — Jacqueline Brazin
(74) *Attorney, Agent, or Firm* — Volpe Koenig

(57) ABSTRACT

The invention relates to a discoid sample holder (1), on which a device (2) for carrying out at least one processing step is formed. According to the invention, a slot (3), into which a sampling instrument (4) can be introduced, and means (5) for releasing a sample from the sampling instrument (4) arranged in the receptacle (3), are formed in the sample holder.

14 Claims, 13 Drawing Sheets

(51) Int. Cl.
*A61B 10/02* (2006.01)
*G01N 33/487* (2006.01)
*G01N 1/10* (2006.01)
*G01N 1/08* (2006.01)

(52) U.S. Cl.
CPC ........... *B01L 3/50273* (2013.01); *B01L 3/561* (2013.01); *G01N 1/08* (2013.01); *G01N 1/10* (2013.01); *G01N 1/31* (2013.01); *G01N 33/4875* (2013.01); *B01L 2200/028* (2013.01); *B01L 2300/069* (2013.01); *B01L 2300/0803* (2013.01); *B01L 2400/0409* (2013.01)

(58) Field of Classification Search
USPC ........................................................ 422/68.1
See application file for complete search history.

(56) References Cited

U.S. PATENT DOCUMENTS

| | | | | |
|---|---|---|---|---|
| 2007/0217951 | A1* | 9/2007 | Matsumoto | B01F 11/0008 422/67 |
| 2009/0036764 | A1* | 2/2009 | Rivas | A61B 5/14532 600/365 |
| 2013/0295663 | A1 | 11/2013 | Weight et al. | |

FOREIGN PATENT DOCUMENTS

| | | |
|---|---|---|
| EP | 2602333 | 6/2013 |
| RU | 2200945 | 3/2003 |

\* cited by examiner

ANALYSIS METHOD, DISCOID SAMPLE HOLDER AND USE OF A SAMPLE HOLDER

BACKGROUND

The invention relates to an analysis method for a sample chamber, involving picking up the sample with a sampling instrument and carrying out at least one processing step on the sample on a discoid sample holder.

Such methods are known and are, for example, used to detect and to analyze the presence of selected substances and/or microorganisms on a surface. To this end, a sample is picked up from the surface using the sampling instrument, for example a swab, and then analyzed by means of a processing step tailored to the particular analysis or multiple processing steps of this kind.

The invention further relates to a discoid sample holder having means for carrying out at least one processing step on a sample.

The use of discoid sample holders has been found to be effective in the automation of processing steps.

The invention lastly relates to the use of a discoid sample holder in an analysis method.

SUMMARY

It is an object of the invention to simplify the handling in an analysis method for a sample.

This object is achieved using one or more features of the invention. In particular, in order to achieve the stated object for an analysis method of the type mentioned at the start, it is thus proposed that the sampling instrument containing the picked-up sample be inserted into a slot of the sample holder and that the sample be detached from the sampling instrument and provided for the at least one processing step. This has the advantage of it being possible to carry out a detachment of the sample from the sampling instrument in or at the sample holder. It is thus possible to dispense with an intermediate treatment of the sample between the pick-up of the sample from the already mentioned surface and the performance of the processing step on the sample. The handling in the analysis method is thus simplified, especially since it is possible to execute all the process steps from pick-up of the sample on the sampling instrument in or at the sample holder. This makes it possible, for example, to form the sampling instrument and the sample holder as disposable parts usable for single use. This makes it possible to better satisfy hygiene and/or cleanliness requirements.

In one embodiment of the invention, it can be envisaged that the sample is detached from the sampling instrument by a movement of the sample holder. This has the advantage of it being possible to dispense with use of additional substances for the detachment of the sample from the sampling instrument. The movement can, for example, be a shaking or swinging movement. In this connection, it is particularly beneficial when the sample is detached from the sampling instrument by a rotation of the sample holder. It has been found that, due to the rotation and the resulting centrifugal forces, it is possible to achieve a particularly efficient detachment of the sample from the sampling instrument.

In one embodiment of the invention, it can be envisaged that the detached sample is gathered in a chamber before the at least one processing step. This has the advantage of it being possible for the completely detached sample after completion of the detachment to be immediately fed to the at least one processing step. A further advantage is that the sample holder can be stopped after the detachment. This is especially beneficial when the detachment is effected by the already mentioned rotation, since then the at least one processing step does not necessarily need to be executed under the influence of centrifugal forces.

In one embodiment of the invention, it can be envisaged that an already detached sample portion is mixed in the chamber with a collection liquid during the detachment. This has the advantage of it being possible to avoid or at least to reduce an excessively strong adhesion of the detached sample to a wall of the chamber. A further advantage is that it is possible to provide the sample in a collection liquid for the at least one processing step.

In one embodiment of the invention, it can be envisaged that an external conveying pressure is applied to the chamber after detachment of the sample in order to convey the detached sample for the at least one processing step. For this purpose, preference is given to stopping or ending the movement of the sample holder. This has the advantage of it being possible to achieve a defined flow situation for carrying out the processing step.

In one embodiment of the invention, it can be envisaged that the slot is outwardly closed after insertion of the sampling instrument. This has the advantage of it being possible to prevent the sampling instrument from falling out during movement of the sample holder. This has the further advantage of it being possible to prevent the detached sample from flowing out of the slot. In this connection, it is particularly beneficial when the slot is closed in a liquid-tight and/or gas-tight manner, for example by the use of an adhesive strip and/or by the use of a stopper or a closure. This has the advantage of it being possible to apply an already mentioned external conveying pressure to the slot in order to output the detached sample as completely as possible. Alternatively or additionally, it can be envisaged that the insertion opening is closable and/or is closed using a closure formed on the sampling instrument.

In one embodiment of the invention, it can be envisaged that the at least one processing step is a cytometry method. This has the advantage of it being possible to establish the presence and/or the number of microorganisms in the sample in a simple manner in the processing step.

In one embodiment of the invention, it can be envisaged that the detached sample is filtered before entry into a chamber, for example the already mentioned chamber. This has the advantage of it being possible for constituents of the sampling instrument which additionally become loose during the detachment process to be kept away from the at least one processing step.

In one embodiment of the invention, it can be envisaged that a swab is used as sampling instrument. Thus, the sample can be particularly easily picked up from a surface. In this connection, it is particularly beneficial when the swab has a swab head formed from tiny hairs protruding from a solid core. It has been found that it is possible to particularly effectively detach the sample from such tiny hairs. One possible reason may be that the tiny hairs, in contrast to conventional sampling materials, are arrangeable or arranged on the core in a non-intertwined manner, and so it is possible to particularly easily detach a picked-up sample by movement processes and/or centrifuge processes.

In one embodiment of the invention, it can be envisaged that the sampling instrument is positioned by the slot at an angle to a radial direction with respect to a center of rotation of the discoid sample holder. In this connection, the slot can lie in a plane defined by the sample holder or else enclose an angle with said plane. Thus, it is possible to avoid that a coupling or a coupling of the sample holder causes an obstacle upon insertion of the sampling instrument.

Alternatively or additionally, it can be envisaged in one embodiment of the invention that the sampling instrument is positioned by the slot from an insertion opening, especially at an outer edge of the discoid sample holder, past a center of rotation, for example the already mentioned center of rotation, and up to the slot end or a slot end on an opposite side of the center of rotation. What is thus achievable is that the sample is detached from the sampling instrument toward the slot end when the sample holder is, for example, centrifuged.

In one embodiment of the invention, it can be envisaged that the sample on the sampling instrument in an absorbent sampling material is inserted into the slot. This has the advantage of it being possible to easily execute secure transport from the pick-up site to the sample holder. In this connection, it is particularly beneficial when the sampling material is pre-moistened, i.e., has a moisture content before the pick-up of the sample. What can thus be easily achieved is that it is possible to easily detach the sample from the sampling material.

The stated object is achieved according to the invention in the case of a discoid sample holder by the features of the additional independent claim directed to a discoid sample holder. In particular, in order to achieve the stated object for a discoid sample holder of the type described at the start, it is thus proposed according to the invention that a slot for a sampling instrument bearing a sample be formed and that means for the detachment of the sample from the sampling instrument be formed. This has the advantage of it being possible to execute a detachment of the sample from the sampling instrument in the discoid sample holder. It is thus possible to dispense with intermediate steps between, firstly, the pick-up of the sample from a surface or from another sampling site and, secondly, the at least one processing step in the sample holder, which intermediate steps have to proceed outside the sample holder. This considerably simplifies the handling of the sample holder in an analysis method according to the invention.

In one embodiment of the invention, it can be envisaged that the means for detachment comprise a coupling for the motion-fixed coupling of the sample holder to a drive. This has the advantage of it being possible to execute in an automated manner a mechanical detachment of the sample, it being possible to dispense with additional substances for the purposes of detachment. In this connection, it is particularly beneficial when the coupling is formed for rotationally fixed coupling to a rotary drive. This has the advantage of it being possible to develop centrifugal forces which bring about a particularly efficient detachment of the sample from the sampling instrument.

In one embodiment of the invention, it can be envisaged that the coupling is formed for rotationally fixed coupling to a rotary drive and that the slot extends from an outwardly open insertion opening to a slot end, with a radial distance of the slot from a center of rotation along the slot between the insertion opening and the slot end, which center of rotation is defined by the coupling, assuming a minimum value. What is thus easily achievable is that the slot end is arranged radially further out with respect to the center of rotation than the slot in the region of the mentioned minimum value. Thus, it is possible to prevent the sample detached at the slot end from flowing back to the insertion opening during a rotation.

In one embodiment of the invention, it can be envisaged that the slot for an insertion of the sampling instrument is oriented in a disk plane predefined by the sample holder or at an acute angle to said plane. This has the advantage of it being possible to provide a compact outer dimension of the sample holder with inserted sampling instrument. In this connection, it is particularly beneficial when the acute angle is less than 45°. In the case of an angle of 0°, the sampling instrument is thus inserted in the disk plane. What is thus generally achieved in this embodiment is that an axial dimension of the sample holder with plugged-in or inserted sampling instrument is small, especially in comparison with a diameter of the sample holder.

In one embodiment of the invention, it can be envisaged that the slot opens into a chamber, especially the already mentioned chamber. This has the advantage of it being possible to collect and to gather the detached sample before the at least one processing step. In this connection, it is particularly beneficial when the chamber is arranged after a slot end, especially the already mentioned slot end, of the slot in a flow direction of the detached sample. This has the advantage of it being possible to easily carry out a gathering-up of the sample in the chamber. Especially in the case of a coupling formed for a rotationally fixed coupling to a rotary drive, it is beneficial when the chamber is arranged radially with respect to a center of rotation of the coupling beyond the slot end. This has the advantage of the occurring centrifugal forces bringing about a flow direction of the detached sample toward the chamber.

In one embodiment of the invention, it can be envisaged that a filter is arranged after the slot in a flow direction, for example in the already mentioned flow direction. This has the advantage of it being possible to keep and/or of keeping fractions or other constituents of the sampling instrument, which have become loose during the detachment process, away from the at least one processing step.

In one embodiment of the invention, it can be envisaged that a resting projection, against which an inserted sampling instrument rests and/or is held in a punctiform or linear fashion, is formed in the slot. This has the advantage of it being possible to avoid a planar resting of the sampling instrument, with the result that it is easily possible to achieve a detachment of the sample from the sampling instrument.

In one embodiment of the invention, it can be envisaged that a cytometer channel connected to the slot is formed. Therefore, the means for carrying out the at least one method step comprise in this case at least the cytometer channel. This has the advantage of it being possible to execute a cytometry method as at least one processing step.

In one embodiment of the invention, it can be envisaged that a liquid reservoir connected to a chamber, especially to the already mentioned chamber, is formed and is filled with a collection liquid. This has the advantage of it being possible to execute a mixing of the detached sample with the collection liquid in the sample holder.

In one embodiment of the invention, it can be envisaged that a pressure connector for an external conveying pressure is formed. This has the advantage of it being possible to easily execute a conveyance of the detached sample to the at least one processing step even in the case of a stationary sample holder.

In one embodiment of the invention, it can be envisaged that the sampling instrument comprises an absorbent sampling material. Thus, the sample holder forms a sample holder set with the sampling material. The use of an absorbent sampling material is particularly beneficial when it is intended that it be possible to pick up a sample from a surface and/or that a sample be picked up from a surface. In this connection, it is particularly beneficial when the sampling material is pre-moistened. In the case of the sample holder set according to the invention, the sampling instrument, for example a swab with the pre-moistened absorbent sampling material, can be packaged and kept ready separately from the sample holder.

In one embodiment of the invention, it can be envisaged that the chamber is formed in a tapered manner in a flow direction of the detached sample. This has the advantage of it being possible to easily execute a gathering of the detached sample. In this connection, it can be envisaged that the flow direction is oriented approximately or exactly radially with respect to a center of rotation of the sample holder. For example, this may be the case when the sample holder is rotated around the center of rotation in order to detach the sample, with the result that the action of a centrifugal force gives rise to the flow direction.

In one embodiment of the invention, it can be envisaged that has an outlet at a chamber end facing away from the slot in a flow direction, for example the already mentioned flow direction, of the detached sample. This has the advantage of it being possible to execute a direct forwarding of the sample to the means for carrying out at least one processing step. If the sample holder is to be rotated during the detachment process, it is beneficial when the outlet is arranged on the chamber radially outward with respect to a center of rotation of the sample holder.

In one embodiment of the invention, it can be envisaged that the slot has a running direction which encloses an angle with a radial direction with respect to a center of rotation of the discoid sample holder. Thus, it is possible to introduce the slot close to a center of rotation, without an insertability of the sampling instrument being reduced.

In one embodiment of the invention, it can be envisaged that the slot runs from an insertion opening past a center of rotation, for example the already mentioned center of rotation, and ends on an opposite side of the center of rotation. This has the advantage of it being possible to avoid a backflow of the detached sample along the sampling instrument. It is particularly beneficial when the insertion opening lies on an outer edge of the discoid sample holder. Thus, it is possible to provide a large length of the slot.

In one embodiment of the invention of possibly independent inventive quality, it can be envisaged that the discoid sample holder has been or is assembled from at least two segments, with each segment being formed as a discoid sample holder according to the invention, especially as described above and/or as claimed in any of the claims directed to a sample holder. This makes it possible to use the individual segments to separately pick up the samples to be analyzed and to then analyze them jointly in the assembled sample holder. It is particularly beneficial when the segments are each separable from one another in pairs along a separation line and an insertion opening of at least one segment lies on the associated separation line. This has the advantage of it being possible to close the insertion opening upon combination of the segments.

Lastly, the stated object is achieved according to the invention by the use of a discoid sample holder according to the invention, especially as described above and/or as claimed in any of the claims directed to a discoid sample holder, in an analysis method according to the invention, especially as described above and/or as claimed in any of the claims directed to an analysis method.

In this connection, it can be envisaged that the sample is picked up using the sampling instrument, that the sampling instrument is inserted into the sample holder, that the sample holder containing the inserted sampling instrument is inserted into an analysis instrument, and that the remaining steps of the analysis method according to the invention are executed on the sample holder in the analysis instrument.

Overall, it can be envisaged that the sample is gathered in a storage chamber of the sample holder after the at least one processing step or after further processing steps. Thus, it is possible for the sample holder together with the sample used to be jointly fed to final disposal.

The invention will now be more particularly elucidated on the basis of exemplary embodiments, but is not limited to these exemplary embodiments. Further exemplary embodiments are revealed by combination of the features of individual or multiple claims with one another and/or with individual or multiple features of the exemplary embodiment.

DETAILED DESCRIPTION OF THE PREFERRED EMBODIMENTS

Figure 1:
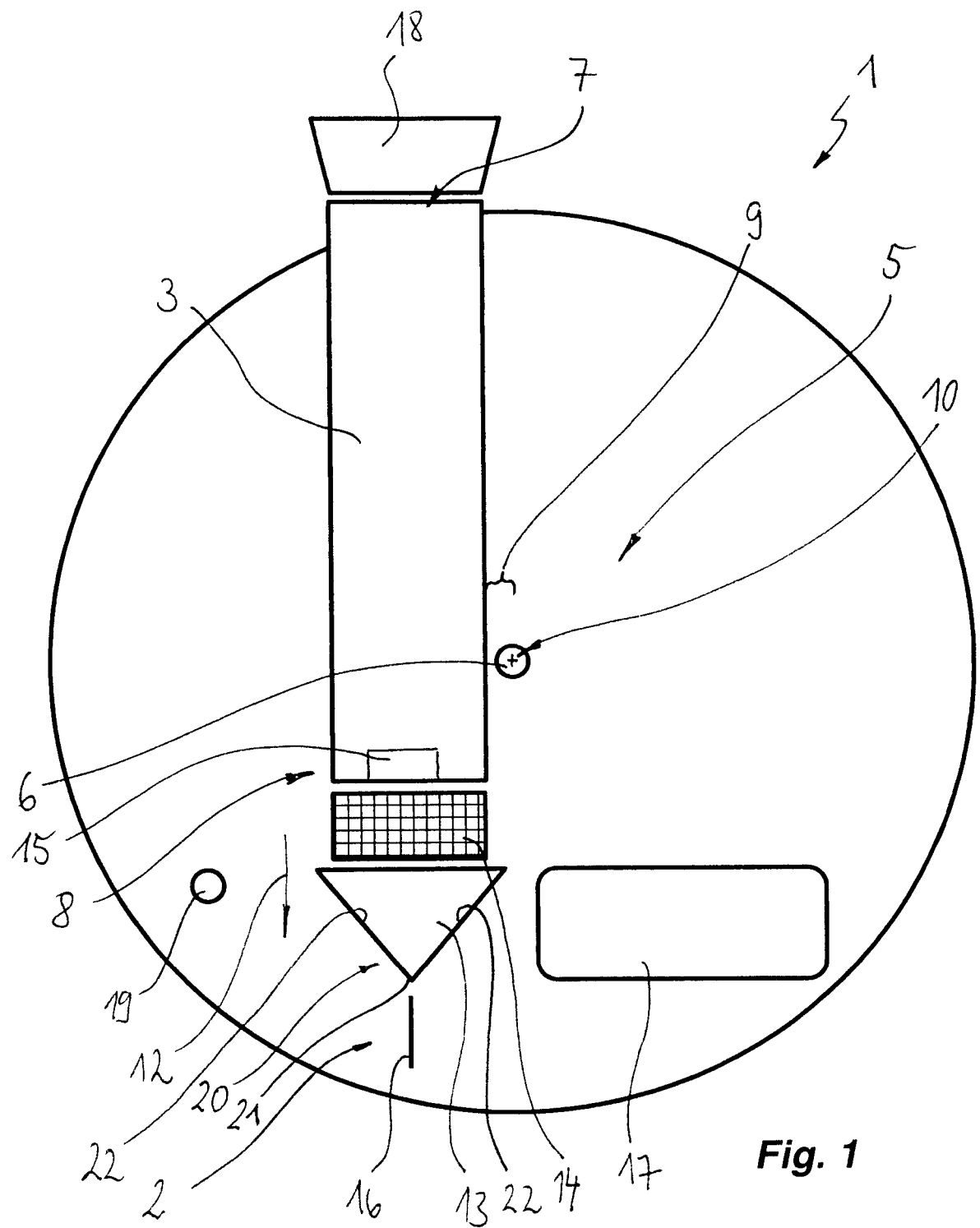
FIG. 1 shows a greatly schematized depiction of a discoid sample holder according to the invention.

A discoid sample holder indicated as a whole by 1 in FIG. 1 comprises means 2, which are to be described in more detail, for carrying out at least one processing step on a sample.

Figure 2:
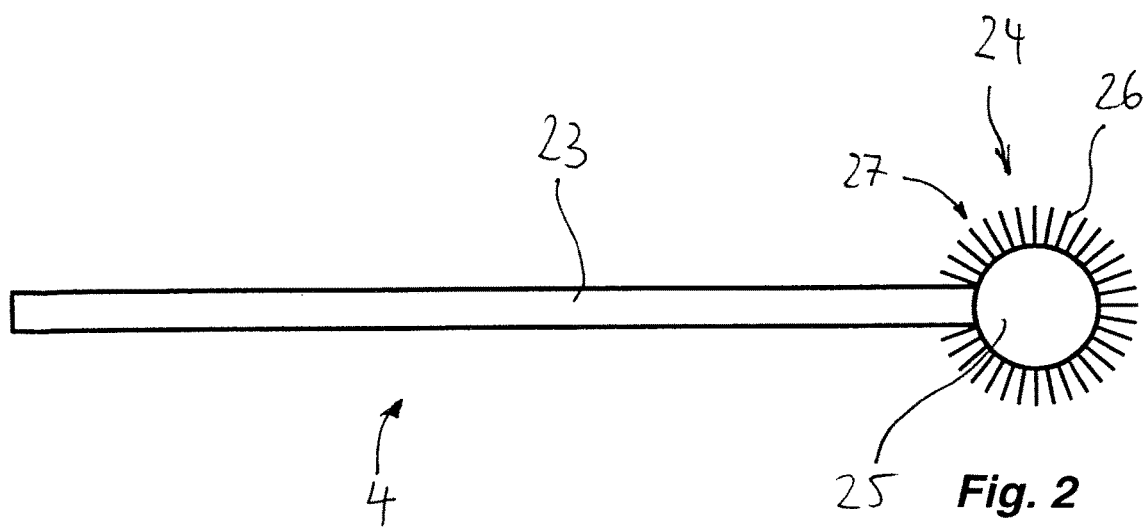
FIG. 2 shows a sampling instrument for use in an analysis method according to the invention.

The sample holder 1 has a slot 3 into which it is possible to insert the already mentioned sample for the at least one processing step on a sampling instrument 4, which is to be described more precisely and is depicted in more detail in FIG. 2.

Therefore, when using the sample holder 1 in the analysis method according to the invention, the sample is picked up with the sampling instrument 4 and then introduced into the slot 3 with the sampling instrument 4.

The sample holder 1 comprises means 5 for the detachment of the sample from the sampling instrument 4 used. This means 5 comprise in particular a coupling 6, by which it is possible to couple the sample holder 1 in a rotationally fixed manner to a rotary drive not depicted further, for example of the already mentioned analysis instrument.

By the use of the rotary drive, the sample holder 1 is rotated in order to detach the sample from the sampling instrument 4 in the slot 3 via the resulting centrifugal force.

In further exemplary embodiments, a general drive is envisaged instead of the rotary drive, it being possible to couple the sample holder 1 in a motion-fixed manner to said general drive via the coupling 6, in order to detach—for example by shaking—the sample from the sampling instrument 4.

The slot 3 in FIG. 1 has an outwardly open insertion opening 7, through which it is possible to insert the sampling instrument 4.

The slot 3 further has a slot end 8, at which the detachment of the sample from the sampling instrument 4 takes place.

Between the insertion opening 7 and the slot end 8, the slot 3 has a straight profile.

In this connection, the arrangement of the slot 3 is such that a variable, radial distance 9 of the slot 3, for example measured in each case from a variable point on a central line of the slot 3, from a center of rotation 10 of the coupling 6 neither at the insertion opening 7 nor at the slot end 8, but between the slot end 8 and the insertion end 7, has a minimum value. What is thus achieved is that the slot end 8 is arranged radially with respect to the center of rotation 10 beyond a section of the slot 3 that is given by said minimum value. Thus, a sample detached from the sampling instrument 4 used does not flow to the insertion opening 7, but to the slot end 8. Thus, the slot 3 runs past the center of rotation 10 from the insertion opening 7, and so the insertion opening 7 lies on one side of the center of rotation 10 and the slot end 8 lies on an opposite side of the center of rotation 10.

Figure 3:
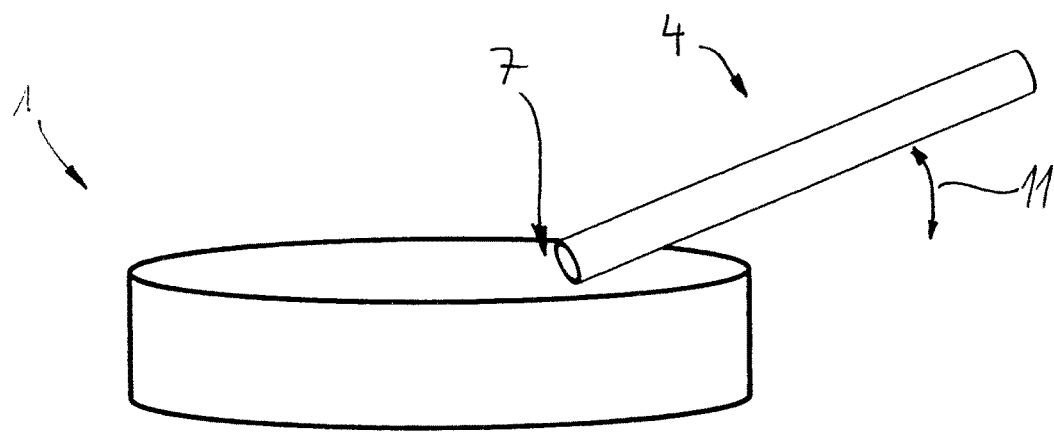
FIG. 3 shows a greatly simplified depiction of the use of a sampling instrument on a sample holder.

FIG. 3 shows the insertion of the sampling instrument 4 into the slot 3 through the insertion opening 7. It is apparent that the sampling instrument 4 is inserted in the sample holder 1 at an acute angle 11, which can be less than 45° for example and is 0° in FIG. 1. In this connection, the slot 3 runs, for example, from the insertion opening 7 up to the opposite side of the sample holder 1. A swab head 24 (cf. FIG. 2) and the end of the swab handle, remote therefrom, of a sampling instrument 4 are thus arranged in the slot 3 on opposing sides. The inserted sampling instrument 4 thus runs past the center of rotation 10.

Upon rotation of the sample holder 1 around the center of rotation 10 with an inserted sampling instrument 4, the centrifugal forces define a flow direction 12.

After the slot end 8 of the slot 3 in the flow direction 12, there is arranged a chamber 13 into which the slot 3 opens.

The chamber 13 serves to collect the detached sample during the rotation of the sample holder 1.

After the slot end 8, there is formed in the flow direction 12 between the slot 3 and the chamber 13 a filter 14, by means of which it is possible to collect non-liquid constituents of the sampling instrument 4, i.e., fragments or fibers for example, and to retain them away from the chamber 13.

Formed in the slot 3 at the slot end 8 is a resting projection 15, against which the sampling instrument 4 in the slot 3 can rest.

In relation to this, the resting projection 15, which is depicted only symbolically, is shaped such that the sampling instrument 4 rests and is held is a punctiform or linear fashion. For example, the resting projection 15 can comprise in relation to this a tip or ridges.

In the exemplary embodiments shown, the means 2 for carrying out the at least one processing step comprise a cytometer channel 16, by which it is possible to execute in a manner known per se an optical cytometry method.

In relation to this, there are arranged on the sample holder 1 an external light source and an external light detector of the analysis instrument, which are known per se and are not further depicted here.

The sample holder 1 comprises a liquid reservoir 17, in which a collection liquid is held available.

In this connection, the liquid reservoir 17 is opened or openable in relation to the chamber 13, and so it is possible to introduce the collection liquid from the liquid reservoir 17 into the chamber 13. The filled chamber 13 is thus prepared for the collection of the detached sample from the sampling instrument 4. Thus, in the chamber 13, the collected sample is mixed with the collection liquid from the liquid reservoir 17. This can take place during the detachment, i.e., after only a fraction of the sample has reached the chamber 13, or after the detachment of the sample.

During the rotation of the sample holder 1, the sampling instrument 4 and/or the detached sample is/are prevented from exiting the slot 3 through the insertion opening 7 by using a stopper 18 to close the insertion opening 7. Instead of the stopper 18, it is also possible to use an adhesive strip or, in general, a closure. In this connection, the sample holder 1 drawn circularly in FIG. 1 can have a flattening, for example by a secant, on which the insertion opening 7 is formed and which is coverable with a planar adhesive strip.

Alternatively or additionally, in a further exemplary embodiment, the sampling instrument 4 can be provided with a closure for closing the insertion opening 7.

Formed on the sample holder 1 is a pressure connector 19 for an external conveying pressure, which connector is connected to the chamber 13, for example via the slot 3. Thus, it is possible to convey a sample collected in the chamber 13 to the cytometer channel 16.

It is apparent in FIG. 1 that the chamber 13 is, in the flow direction 12, preferably tapered in a radially outward manner.

Formed on a chamber end 20, which is situated on a side of the chamber 13 that is facing away from the slot 3, is an outlet 21, which is connected to the cytometer channel 16 or, in general, to the means 2 for carrying out a processing step.

The outwardly tapered shape of the chamber 13 thus forms walls 22 of the chamber 13 which feed the collected sample to the processing step.

FIG. 2 shows a sampling instrument 4 in the form of a swab 23 having a swab head 24.

The swab head 24 bears an absorbent sampling material 27, which is contacted with the sample to be picked up.

In this connection, the swab head 24 comprises a solid core 25 and tiny hairs 26 protruding from said solid core 25.

The tiny hairs 26 form the sampling material 27 and, in this connection, protrude outwardly from the core 25. They are not interwoven or intertwined.

Thus, the picked-up sample can be easily detached from the tiny hairs 26 by shaking or by a centrifugal force, once the sampling instrument 4 is situated in the slot 3.

The use of the sampling instrument 4 as per FIG. 2 in the sample holder 1 takes place according to the invention as follows:

Firstly, the sample is picked up from a surface using the sampling instrument 4 and inserted into the slot 3 with the sampling instrument 4.

Then, the sample holder 1 is coupled to a rotary drive via the coupling 6, for example by insertion of the sample holder 1 into a corresponding analysis instrument.

Then, the slot 3 is outwardly closed at the insertion opening 7 in a gas-tight and liquid-tight manner by a stopper 18 or by a different closure.

Figure 4:
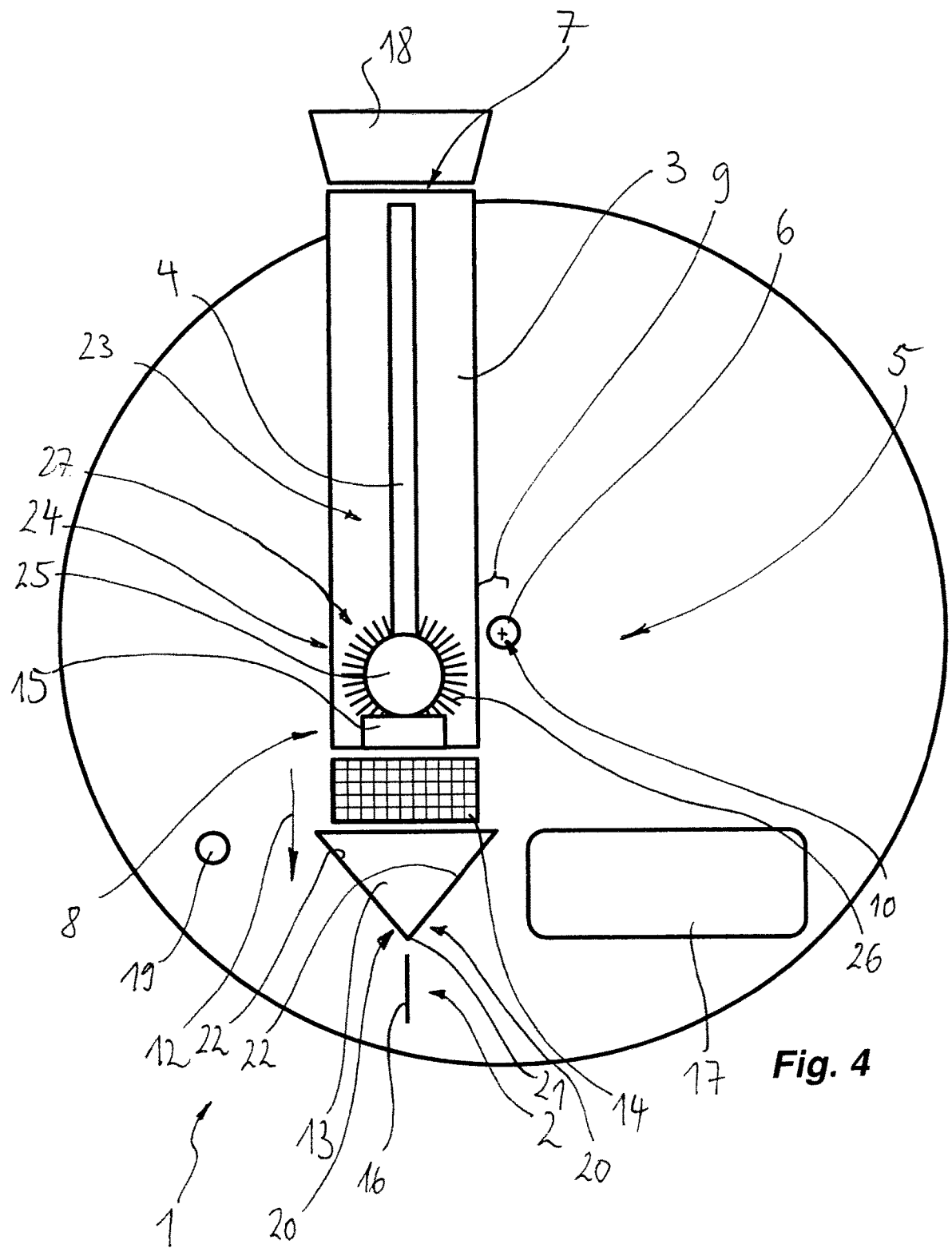
FIG. 4 shows the sample holder, as per FIG. 1, with inserted sampling instrument.

FIG. 4 shows the situation after closure of the insertion opening 7 and before the start of the rotation.

In a next step, the sample holder 1 is made to rotate, and so the centrifugal force detaches the sample from the sampling material 27, from the sampling instrument 4 and in particular the swab head 24.

This sample is fed, at the slot end 8, through a filter 14 to the chamber 13, where it is gathered. In the chamber 13, the collected sample is mixed with a collection liquid on the liquid reservoir 17.

Subsequently, the sample holder 1 is stopped and an external conveying pressure is applied to the pressure connector 19.

This external conveying pressure is applied to the chamber 13 via the slot 3 in order to feed the collected sample to the means 2 for carrying out the at least one processing step.

In this connection, in the exemplary embodiment, the sample is conveyed through a cytometer channel 16 in order to execute a cytometry method.

Figure 5:
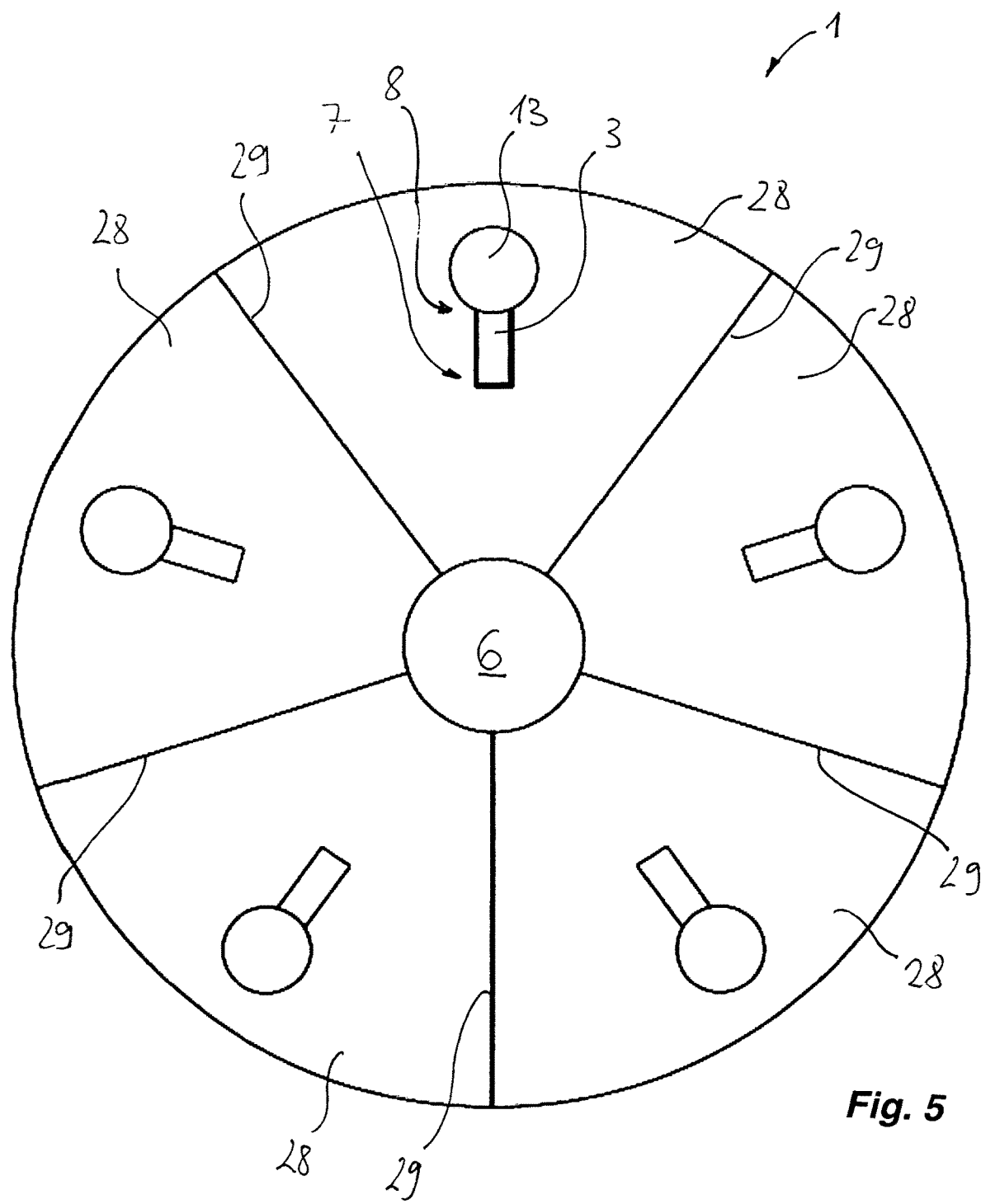
FIG. 5 shows a further sample holder according to the invention, assembled from five discoid sample holders in the form of segments.

FIG. 5 shows a further sample holder 1 according to the invention, consisting of segments 28 assembled at separation lines 29. Components and functional units which are identical or similar in function or construction to the preceding exemplary embodiments are indicated by the same reference signs and not described separately. The explanations in relation to FIGS. 1 to 4 therefore apply mutatis mutandis to FIGS. 5 to 8.

Figure 6:
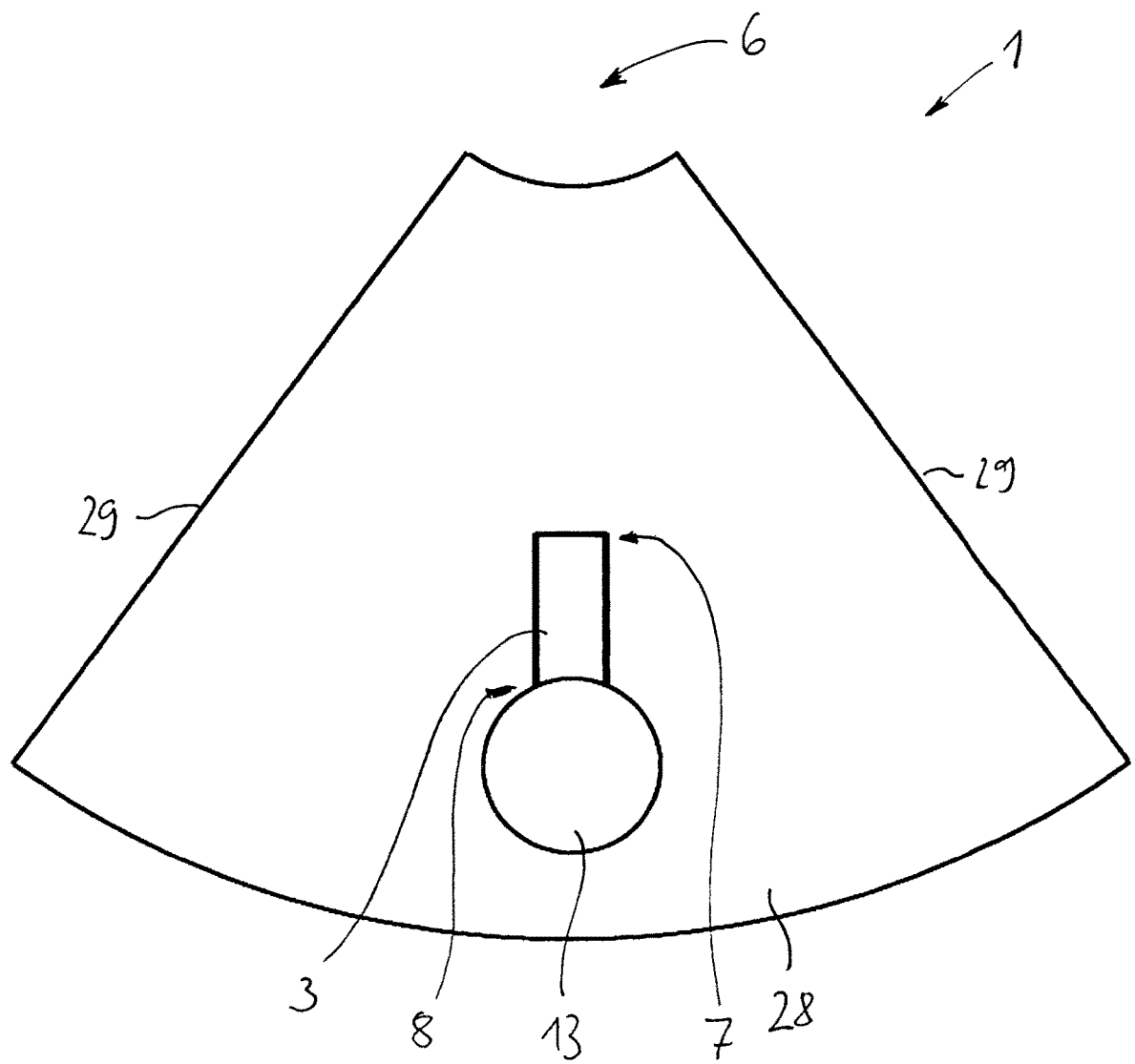
FIG. 6 shows a segment from FIG. 5.
Figure 7:
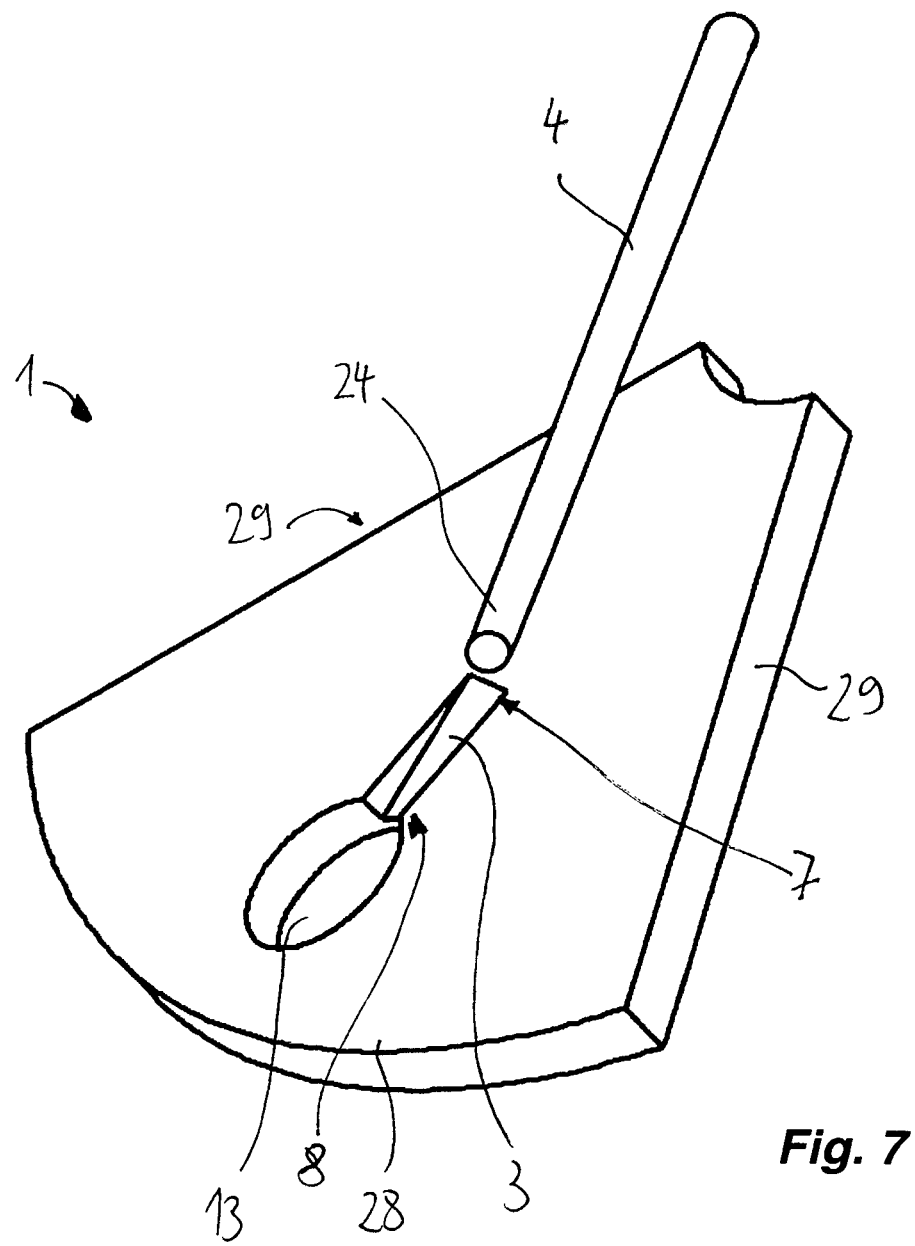
FIG. 7 shows the insertion of a sampling instrument into the segment from FIG. 6.
Figure 8:
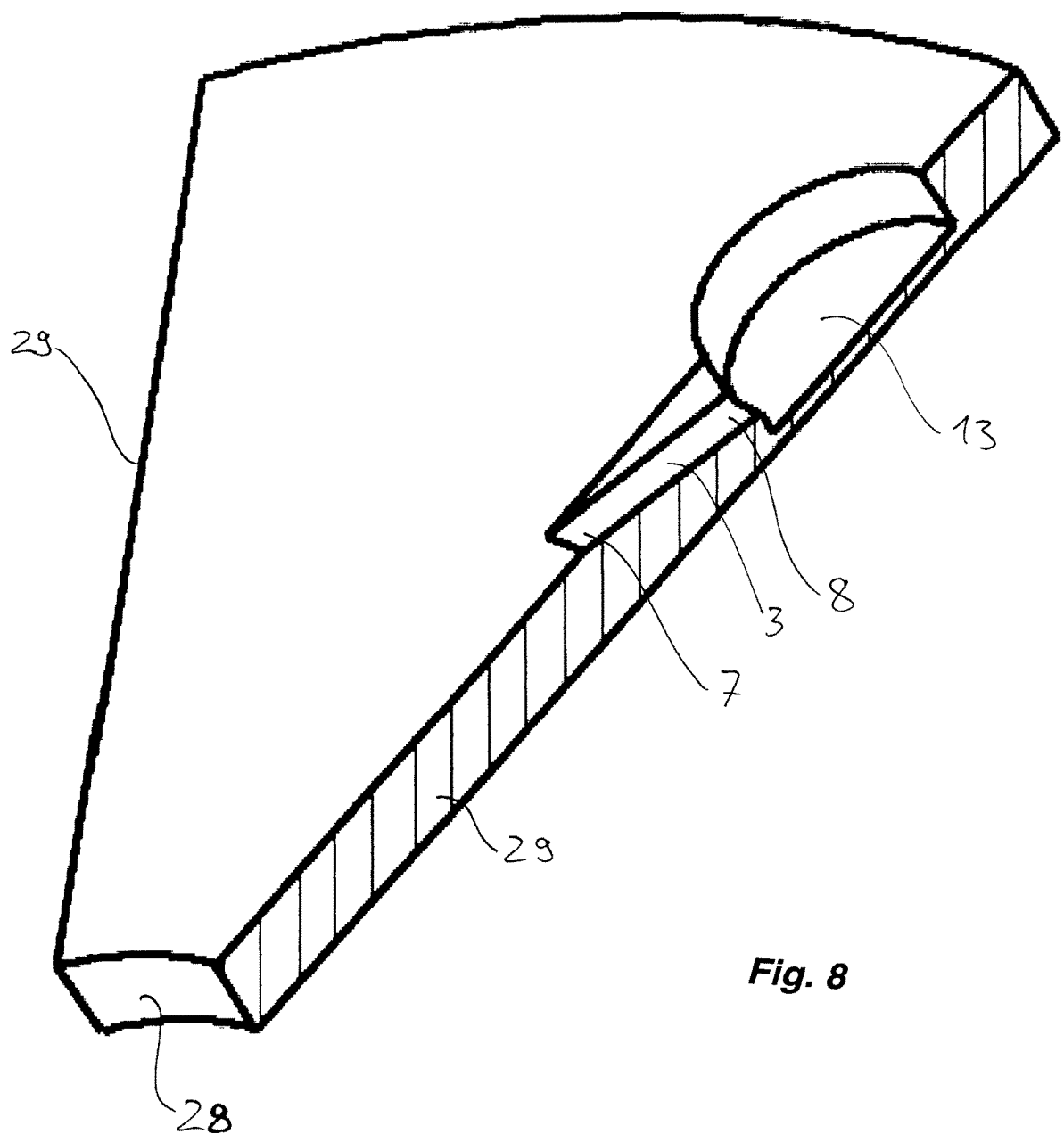
FIG. 8 shows a sectional representation through the segment from FIG. 6.

Each segment 28, taken individually, forms a sample holder 1 according to the invention, which sample holder is illustrated in FIGS. 6 to 8 and is in each case formed such that it is assemblable with further sample holders 1 according to the invention (segments 28) to form a circular disk as per FIG. 5. In particular, each segment is provided with preferably radially running separation lines 29 in order to allow combination.

The slots 3 are each oriented radially and allow an insertion of the sampling instrument 4 from outside of a plane defined by the sample holder 1, cf. FIG. 7.

FIG. 8 shows that the running direction of the slot 3 encloses an angle with the disk plane.

Figure 9:
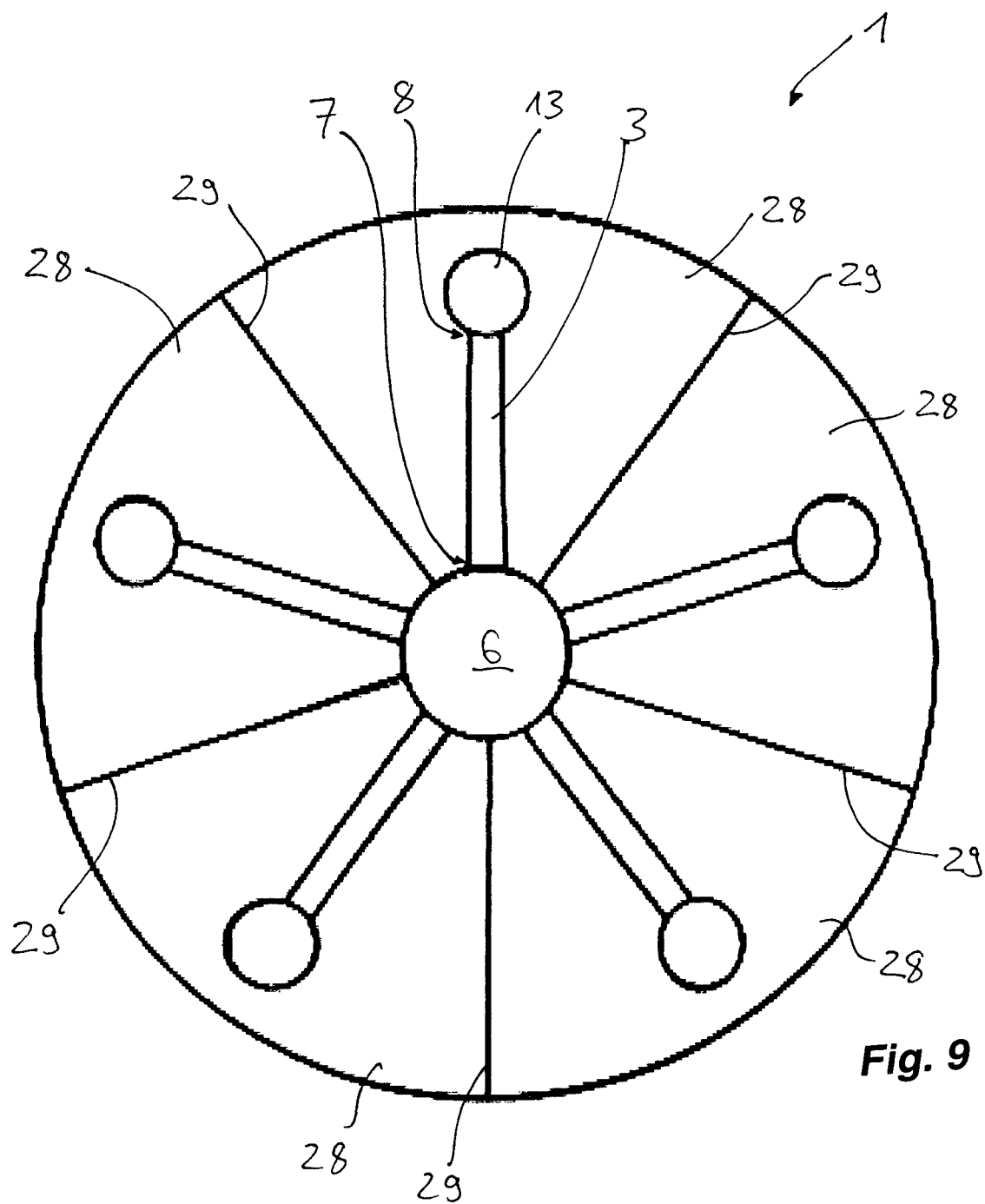
FIG. 9 shows a further sample holder according to the invention, assembled from five discoid sample holders in the form of segments, having slots running radially away from the center of rotation.
Figure 10:
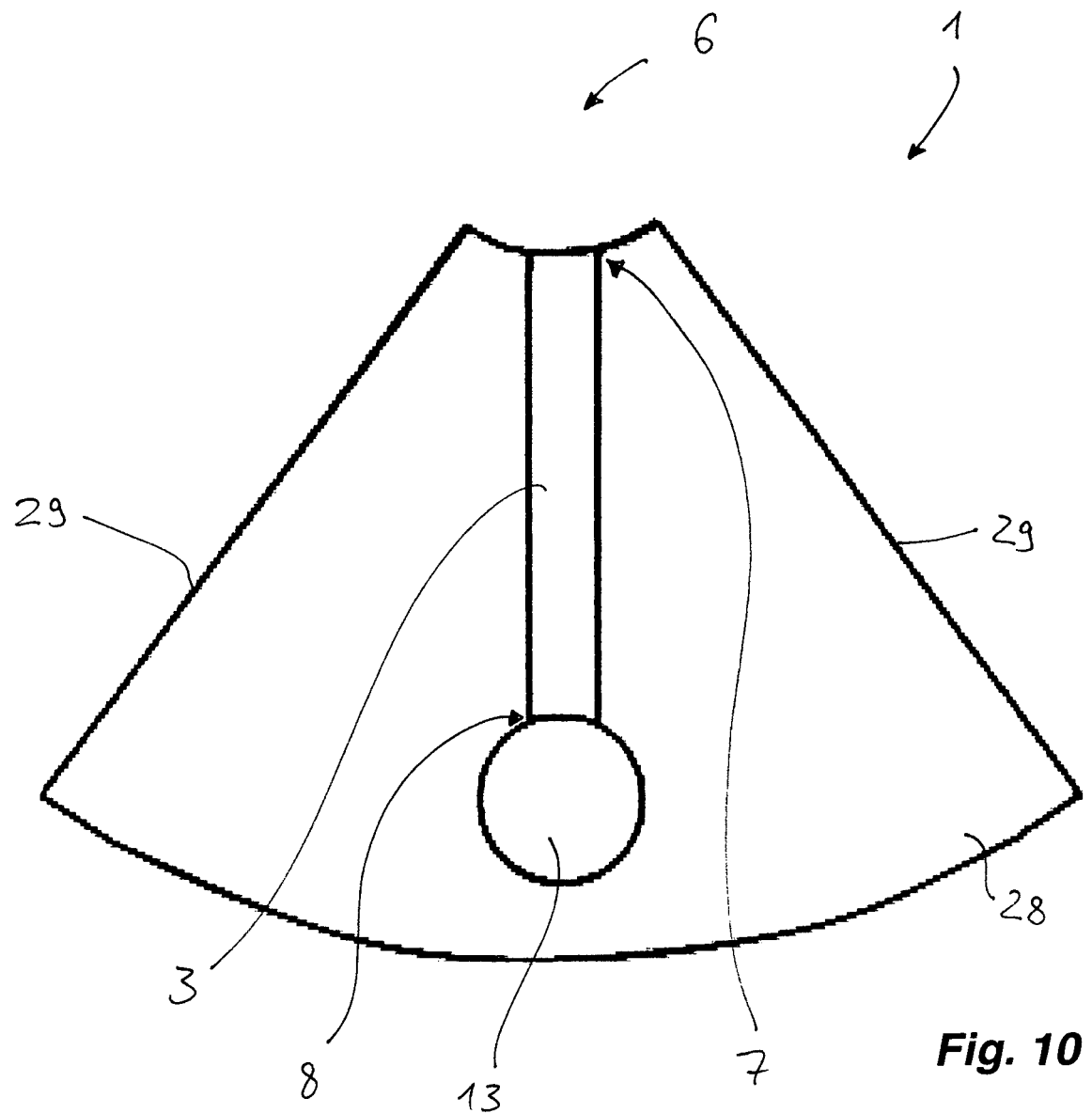
FIG. 10 shows a segment from FIG. 9.
Figure 11:
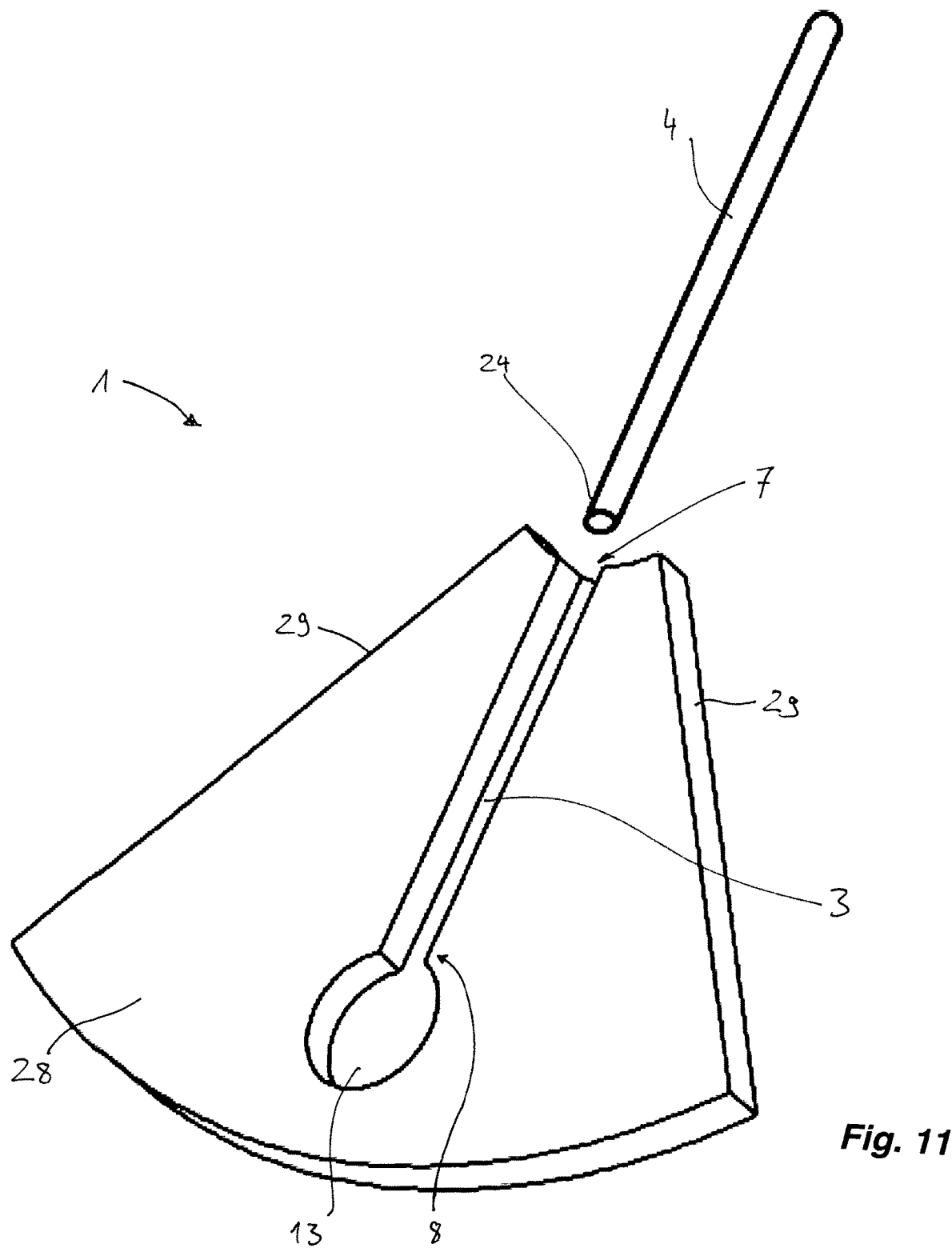
FIG. 11 shows the insertion of a sampling instrument into the segment from FIG. 10.

FIG. 9 shows a further sample holder 1 according to the invention, formed of segments 28 assembled at separation lines 29. Components and functional units which are identical or similar in function or construction to the preceding exemplary embodiments are indicated by the same reference signs and not described separately. The explanations in relation to FIGS. 1 to 8 therefore apply mutatis mutandis to FIGS. 9 to 11.

The slots 3 are each directed up to the coupling 6. An insertion of the sampling instrument is thus possible in the disk plane of the sample holder 1 before the segments 28 are assembled. The assembled sample holder 1 in FIG. 9 thus has a star-shaped arrangement of slots 3.

Figure 12:
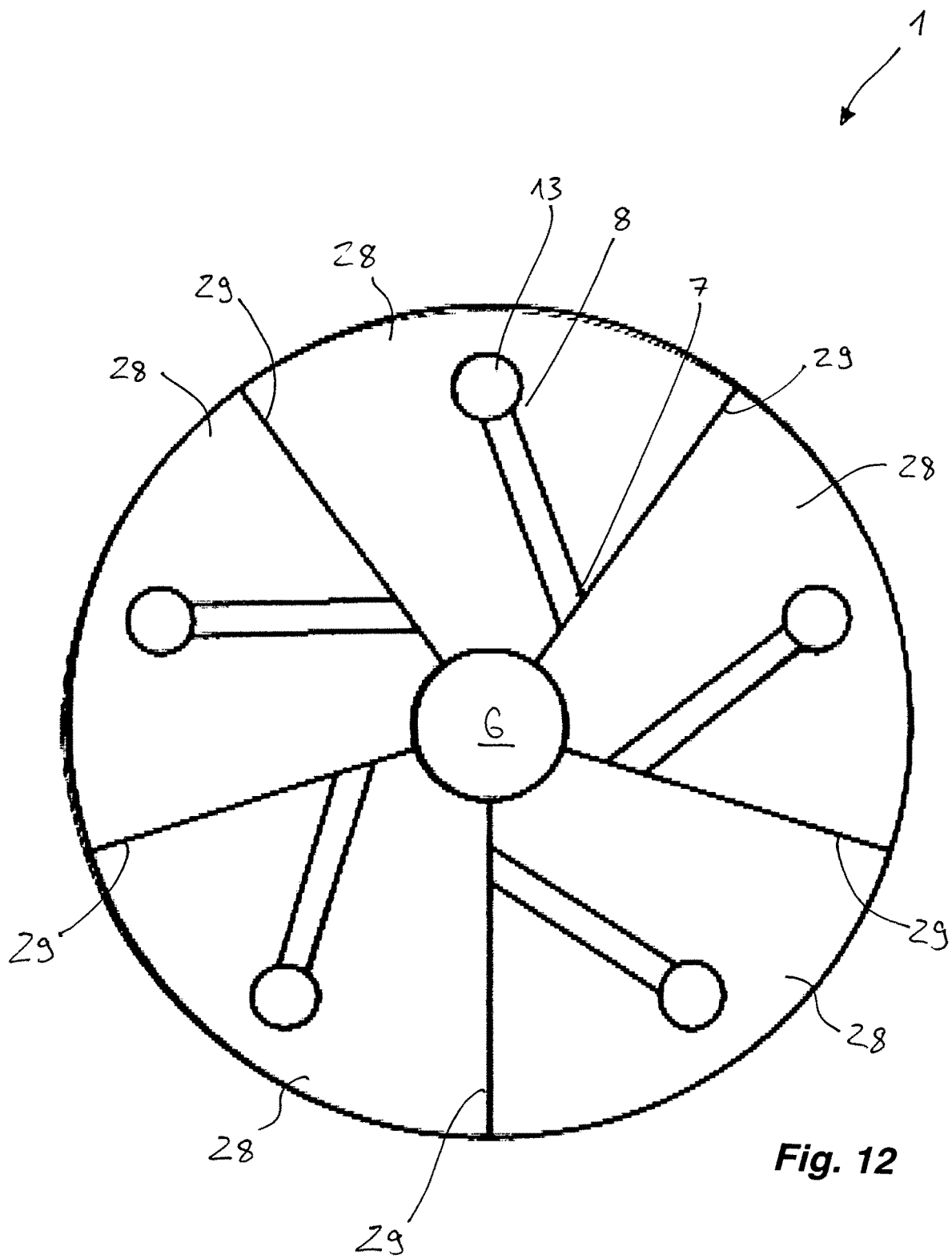
FIG. 12 shows a further sample holder according to the invention, assembled from five discoid sample holders in the form of segments, having slots running diagonally at an angle to the radial direction.
Figure 13:
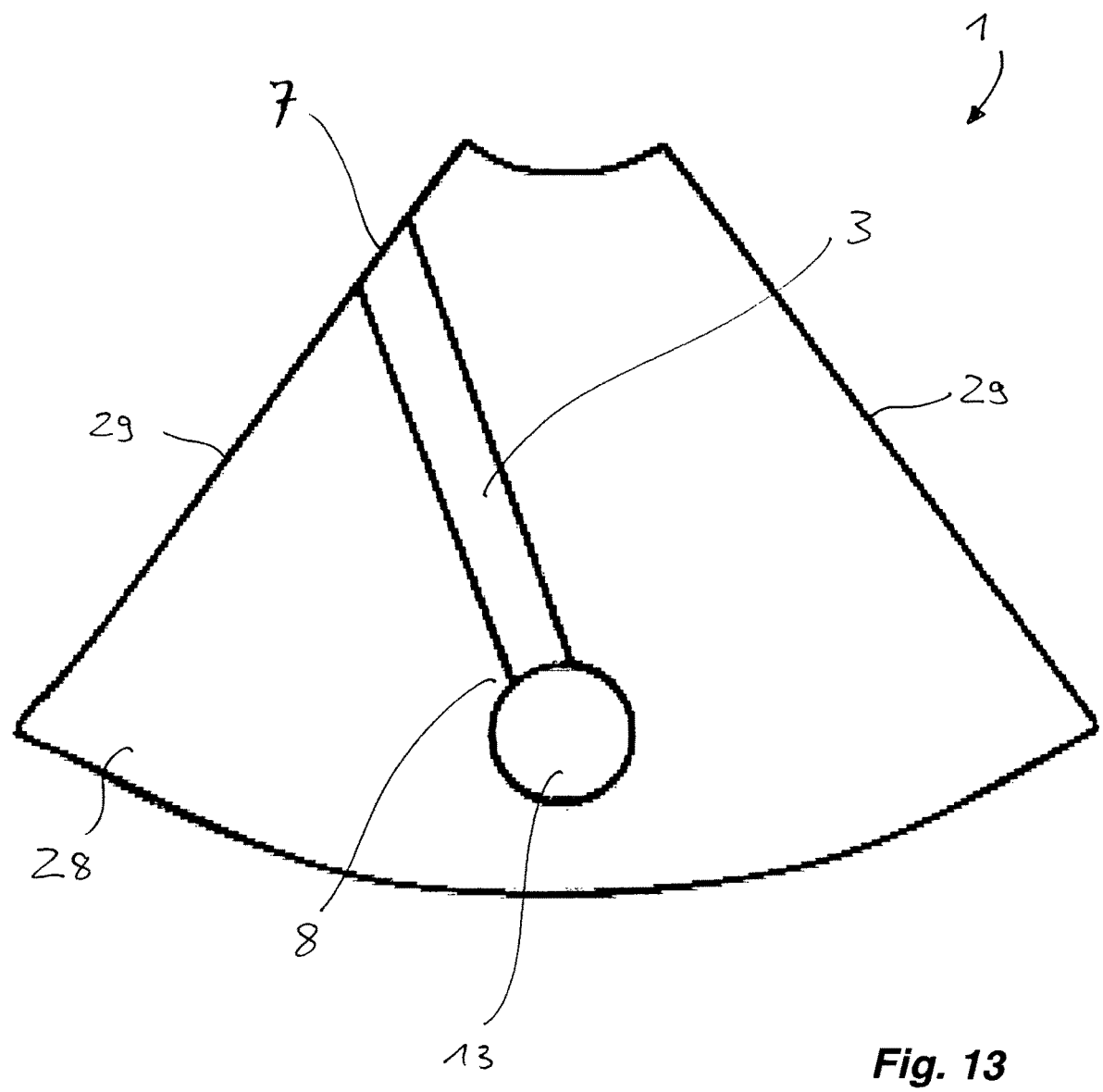
FIG. 13 shows a segment from FIG. 12.
Figure 14:
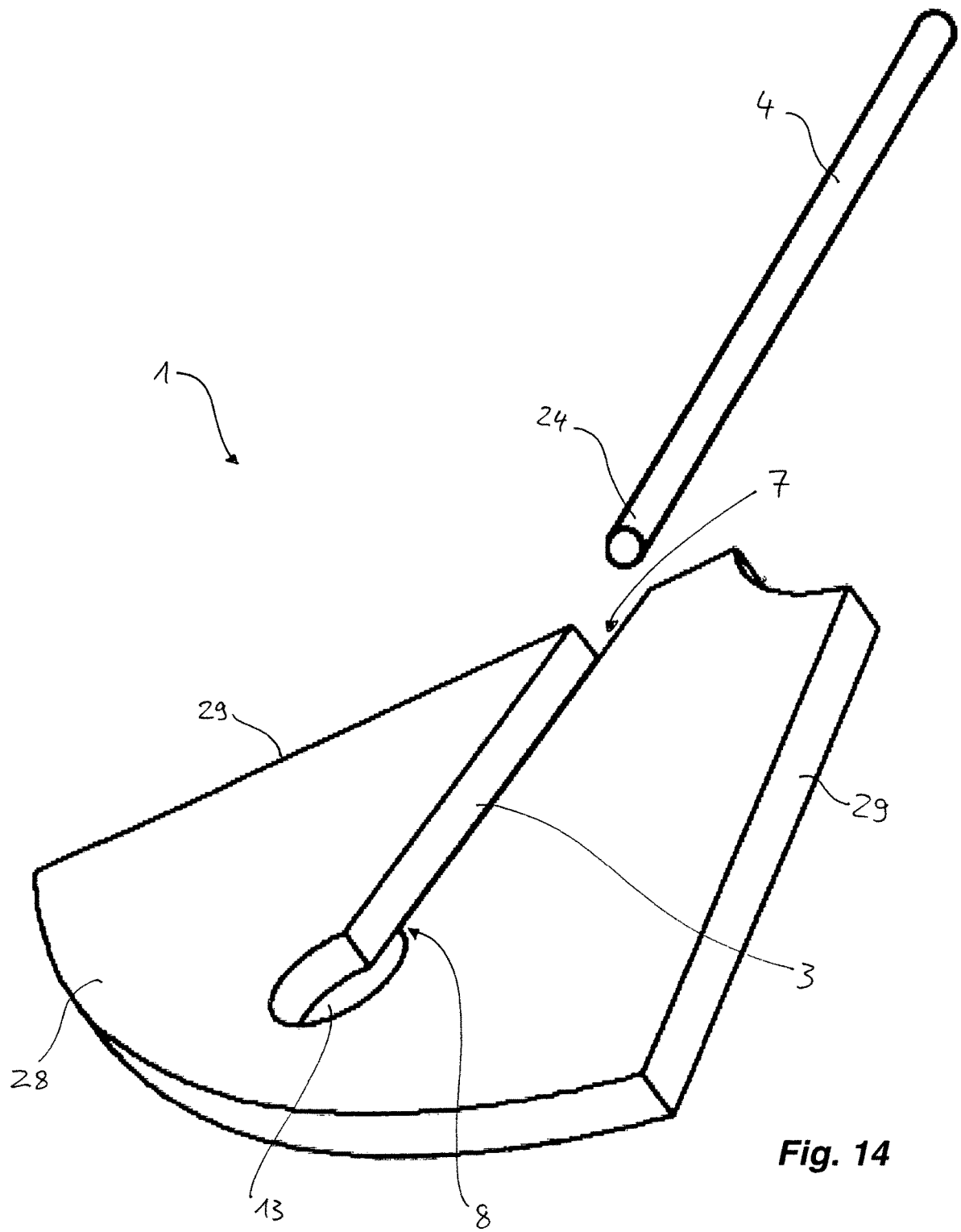
FIG. 14 shows the insertion of a sampling instrument into the segment from FIG. 13.

FIG. 12 shows a further sample holder 1 according to the invention, formed of segments 28 assembled at separation lines 29. Components and functional units which are identical or similar in function or construction to the preceding exemplary embodiments are indicated by the same reference signs and not described separately. The explanations in relation to FIGS. 1 to 11 therefore apply mutatis mutandis to FIGS. 12 to 14.

In this connection, the slots 3 each run from the separation line 29 to a slot end 8, with the running direction of the slots 3 each enclosing an angle with the radial direction pointing to the center of rotation. The insertion openings 7 are closed in an assembled sample holder 1 by the adjacent segment 28.

In the exemplary embodiments that are shown as per FIGS. 5 to 14, the segments 28 of a sample holder 1 are each identical. However, it is also possible to combine different segments 28, or it is possible, as a deviation from what has been shown, to assemble shaped segments to form sample holders comprising less than five or more than five segments.

In the case of the discoid sample holder 1 on which means 2 for carrying out at least one processing step are formed, it is provided to form a slot 3, in which it is possible to insert a sampling instrument 4, and means 5 for the detachment of a sample from the sampling instrument 4 arranged in the slot 3.

The invention claimed is:

1. An analysis method for a sample, comprising:
   picking up the sample with a sampling instrument (4) and carrying out at least one processing step on the sample on a discoid sample holder (1), including
   inserting the sampling instrument (4) containing the picked-up sample into a slot (3) of the sample holder (1)
   wherein the slot (3) is oriented at an angle of less than 45° to a disk plane predefined by the discoid sample holder (1) and
   detaching the sample from the sampling instrument (4) in the slot (3) for the at least one processing step, wherein the sample is detached from the sampling instrument (4) in the slot (3) by centrifugal force created due to a rotation of the sample holder (1), wherein
   the sampling instrument (4) is rotated together with the sample holder (1) and
   the sampling instrument (4) is positioned by the slot (3) at an angle to a radial direction with respect to a center of rotation (10) of the discoid sample holder (1), such that the sample detached from the sampling instrument (4) is prevented from flowing back to an insertion opening (7) of the slot (3) when the sample holder (1) is rotated.

2. The analysis method as claimed in claim 1, further comprising gathering the detached sample in a chamber (13) before the at least one processing step, and mixing the detached sample in the chamber (13) with a collection liquid during the detaching.

3. The analysis method as claimed in claim 2, further comprising at least one of applying an external conveying pressure to the chamber (13) after detachment of the sample in order to convey the detached sample for the at least one processing step or closing the slot (3) after insertion of the sampling instrument (4), using at least one of an adhesive strip, a stopper (18), or by use of a closure formed on the sampling instrument (4).

4. The analysis method as claimed in claim 1, wherein the at least one processing step is a cytometry method or the detached sample is filtered before entry into a chamber (13).

5. The analysis method as claimed in claim 1, further comprising using a swab (23) as the sampling instrument (4).

6. The analysis method as claimed in claim 1, wherein the sampling instrument (4) is positioned by the slot (3) from an insertion opening (7) past the center of rotation (10) or past a center of rotation (10) and up to a slot end (8) on an opposite side of the center of rotation (10).

7. The analysis method as claimed in claim 1, wherein the sample on the sampling instrument (4) is held in an absorbent sampling material (27) and inserted into the slot (3).

8. An analysis method for a sample, comprising:
picking up the sample with a sampling instrument (4) and carrying out at least one processing step on the sample on a discoid sample holder (1), including
inserting the sampling instrument (4) containing the picked-up sample into a slot (3) of the sample holder (1), wherein the slot (3) is oriented at an angle of less than 45° to a disk plane predefined by the discoid sample holder (1); and
detaching the sample from the sampling instrument (4) in the slot (3) for the at least one processing step, wherein the sample is detached from the sampling instrument (4) in the slot (3) by a centrifugal force created due to a rotation of the sample holder (1), wherein the sampling instrument (4) is rotated together with the sample holder (1) and wherein, starting from an insertion opening (7) of the slot (3), the sampling instrument (4) is introduced from radially inside to radially outside with respect to a center of rotation (10) of the sample holder (1), such that the sample detached from the sampling instrument (4) is prevented from flowing back to the insertion opening (7) when the sample holder (1) is rotated.

9. The analysis method as claimed in claim 8, further comprising gathering the detached sample in a chamber (13) before the at least one processing step, and mixing the detached sample in the chamber (13) with a collection liquid during the detaching.

10. The analysis method as claimed in claim 9, further comprising at least one of applying an external conveying pressure to the chamber (13) after detachment of the sample in order to convey the detached sample for the at least one processing step or closing the slot (3) after insertion of the sampling instrument (4), using at least one of an adhesive strip, a stopper (18), or by use of a closure formed on the sampling instrument (4).

11. The analysis method as claimed in claim 8, wherein the at least one processing step is a cytometry method or the detached sample is filtered before entry into a chamber (13).

12. The analysis method as claimed in claim 8, further comprising using a swab (23) as the sampling instrument (4).

13. The analysis method as claimed in claim 8, wherein the sampling instrument (4) is positioned by the slot (3) from an insertion opening (7) past the center of rotation (10) or past a center of rotation (10) and up to a slot end (8) on an opposite side of the center of rotation (10).

14. The analysis method as claimed in claim 8, wherein the sample on the sampling instrument (4) is held in an absorbent sampling material (27) and inserted into the slot (3).

* * * * *